United States Patent
Izmailov et al.

(10) Patent No.: US 6,760,668 B1
(45) Date of Patent: Jul. 6, 2004

(54) METHOD FOR ALIGNMENT OF DNA SEQUENCES WITH ENHANCED ACCURACY AND READ LENGTH

(75) Inventors: Alexandre Izmailov, Etobicoke (CA); Henryk Zaleski, Mississauga (CA); Stephen Darasch, Toronto (CA)

(73) Assignee: Bayer HealthCare LLC, Tarrytown, NY (US)

( * ) Notice: Subject to any disclaimer, the term of this patent is extended or adjusted under 35 U.S.C. 154(b) by 0 days.

(21) Appl. No.: 09/536,111

(22) Filed: Mar. 24, 2000

(51) Int. Cl.[7] .................... G06F 19/00; G01N 33/48; C12Q 1/68
(52) U.S. Cl. .................... 702/20; 702/19; 435/6
(58) Field of Search .................... 702/19, 20; 435/6

(56) References Cited

U.S. PATENT DOCUMENTS

| | | | |
|---|---|---|---|
| 5,124,247 A | 6/1992 | Ansorge | |
| 5,273,632 A | 12/1993 | Stockham et al. | |
| 5,365,455 A | 11/1994 | Tibbetts et al. | |

(List continued on next page.)

FOREIGN PATENT DOCUMENTS

| | | |
|---|---|---|
| EP | 91118244.2 | 3/1987 |
| EP | 87305101.5 | 9/1987 |
| EP | 92104984.7 | 3/1992 |
| EP | 93250264.4 | 9/1993 |

OTHER PUBLICATIONS

Sanger, et al; NA Sequencing with Chain–Terminating Inhibitors; Proc.Natl.Acad.Sci.USA; vol. 74, No. 12, Dec. 1977; Medical Research Council Laboratory of Molecular Biology; Cambridge, England.

Bowling, et al.; Neighboring Nucleotide Interactions During DNA Sequencing Gel Electrophoresis; Nucleic Acids Research, vol. 19, No. 11; 1991 Oxford University Press.
Dear, et al.; A Sequence Assembly and Editing Program for Efficient Management of Large Projects; Nucleic Acids Research, vol. 19, No. 14; 1991 Oxford University Press.
Giddings, et al.; An Adaptive, Object Oriented Strategy for Base Calling in DNA Sequence Analysis; Nucleic Acids Research, 1993 vol. 21, No. 19; 1993 Oxford University Press.

(List continued on next page.)

*Primary Examiner*—Marjorie Moran
*Assistant Examiner*—Lori A. Clow
(74) *Attorney, Agent, or Firm*—Holland & Hart LLP (57) ABSTRACT

In order to align DNA sequence data traces, an experimental data trace representing the positions of a first species of base within a target polynucleotide and a reference data trace representing the positions of a second species of base (which may be the same as or different from the first species) within a reference polynucleotide are obtained by separating appropriate sequencing fragments generated from the target and reference polynucleotides on an electrophoresis gel. For each reference data trace, a plurality of peaks corresponding to fragments having a size in the range of 40 to 1200 bases are selected. A base number is assigned to each of the selected peaks in the reference data trace, and a numerical "peak file" is created with information about the peak number and migration time (or distance). This peak file is analyzed to determine a set of polynomial coefficients which will allow substantial linearization of a plot of peak number versus separation between adjacent peaks and alignment of the traces with respect to each other. These coefficients are used to create a corrected time scale identifying where peaks should be located on a given experimental gel. This corrected time scale is used to guide the sampling of the experimental data, and for assignment of peaks within the data.

22 Claims, 6 Drawing Sheets

U.S. PATENT DOCUMENTS

| | | | |
|---|---|---|---|
| 5,666,435 | A | 9/1997 | Burgi et al. |
| 5,710,628 | A | 1/1998 | Waterhouse |
| 5,712,476 | A | 1/1998 | Renfrew et al. |
| 5,733,729 | A | 3/1998 | Lipshutz et al. |
| 5,834,189 | A | 11/1998 | Stevens et al. |
| 5,849,542 | A | 12/1998 | Reeve et al. |
| 5,853,979 | A | 12/1998 | Green et al. |
| 5,891,632 | A * | 4/1999 | Imai ............................. 435/6 |
| 5,916,747 | A | 6/1999 | Gilchrist et al. |
| 5,981,186 | A | 11/1999 | Gabe et al. |
| 6,208,941 | B1 * | 3/2001 | Marks ......................... 702/20 |
| 6,303,303 | B1 * | 10/2001 | Green et al. ................... 435/6 |

OTHER PUBLICATIONS

Golden, et al.; Pattern Recognition for Automated DNA Sequencing: I. On–line Signal Conditioning and Feature Extraction for Basecalling; Vanderbilt University, Nashville, TN.

Koutny, et al.; Automated image Analysis for Distortion Compensation in Sequencing Gel Electrophoresis; Applied Spectroscopy, Jan., No. 1; Frederick, MD.

Wiemann, et al.; Simultaneous On–Line DNA Sequencing on Both Strands with Two Fluorescent Dyes; Analytical Biochemistry 224, 1995; Academic Press, Inc.

Tibbetts, et al.; Neural Networks for Automated Basecalling of Gel–based DNA Sequencing Ladders; Vanderbilt University, Nashville, TN.

* cited by examiner

METHOD FOR ALIGNMENT OF DNA SEQUENCES WITH ENHANCED ACCURACY AND READ LENGTH

BACKGROUND OF THE INVENTION

This application relates to DNA sequencing technology and in particular to a method for alignment of DNA sequences which provides enhanced accuracy and read-length.

DNA sequencing is generally performed today using one of two methodologies: the chemical degradation method or the chain termination method. Of these, the chain termination method originally described by Sanger et al., *Proc. Natl. Acad. Sci. USA* 74: 5463–5467 (1977) or variations thereof have been adopted in many cases for development of automated sequencing instruments and protocols.

In the chain termination sequencing method, fragments are generated using chain termination reagents in a template-dependant polymerization reaction. The lengths of the fragments indicate the positions of one species of base in a target polynucleotide. If fragment sets are generated for each of the four species of bases (A, C, G and T), analysis of the fragment sizes permits the explicit determination of the sequence of the target polynucleotide. While the translation of this conceptual methodology into practice is effective for determination of sequences, the application in automated systems has faced numerous challenges. These include the fact that the band shape produced following electrophoresis of real fragments is not consistent from one band to the next and may not be perfectly straight (smiling may occur); variations which can occur in peak spacing from one lane of a gel to the next; variations in peak spacing which can occur as the length of the run increases; and decreases in resolution which occur as the length of the run increases. Furthermore, since much of the cost associated with DNA sequencing is in the set-up time involved, for clinical and diagnostic applications the larger the length of DNA which can be sequenced with accuracy, the smaller the per patient cost can be. These considerations have led to a variety of proposals for improving the chemistry used in sequencing, or for improving the manner in which data representing the detected sequencing fragment is processed. The present invention relates to the second type of improvement.

In order to obtain meaningful sequence information from raw data obtained by electrophoresis of labeled sequencing fragments, one of the most important factors is the alignment of the data traces representing each species of base. In non-automated systems, this is frequently done by eye-ball, and the eye of a skilled technician is in fact a remarkable tool for this purpose. Commonly assigned U.S. Pat. No. 5,916,747, which is incorporated herein by reference, discloses a method for aligning data traces from four channels of an automated electrophoresis detection apparatus in which each channel detects the products of one of four chain-termination DNA sequencing reactions such that the four channels together provide information concerning the sequence of all four bases within a nucleic acid polymer being analyzed. The method places the four data traces in a trial alignment, and then determines coefficients of shift and stretch for selected data points within each normalized data trace to optimize a cost function which reflects the extent of overlap of peaks in the combined normalized data traces to which the coefficients have been applied. Warp functions are then generated for the normalized data traces from the coefficients of shift and stretch determined for the selected data points, and applied to the respective data trace to produce four warped data traces which are assembled to form an aligned data set. This data set is then used for base-calling to complete the sequence determination process.

The procedure of the '747 patent is generally suited for the determination of sequences where explicit data for the positions of all four bases are obtained. On the other hand, it is not always necessary to determine the positions of all of four species of bases in order to obtain diagnostic information from a given polynucleotide. (See, commonly assigned U.S. Pat. No. 5,834,189, which is incorporated herein by reference). Commonly assigned U.S. Pat. No. 5,853,979, which is incorporated herein by reference discloses a method for the interpretation of experimental fragment patterns for polynucleotides having putatively known sequences. In this method, at least one raw fragment pattern representing the positions of a selected nucleotide base as a function of migration time or distance is obtained for the experimental sample. The fragment pattern is evaluated to determine one or more "normalization coefficients." These normalization coefficients reflect the displacement, stretching or shrinking, and rate of stretching or shrinking of the clean fragment, or segments thereof, which are necessary to obtain a suitably high degree of correlation between the clean fragment pattern and a standard fragment pattern which represents the positions of the selected nucleic acid base within a standard polymer actually having the known sequence as a function of migration time or distance. The normalization coefficients are then applied to the fragment pattern to produce a normalized fragment pattern which is used for base-calling in a conventional manner. As indicated, however, this technique requires prior knowledge of the expected fragment pattern for the polynucleotide being analyzed.

Notwithstanding such techniques, there remains room for improvement in the manner in which automated analysis of sequencing fragment patterns are carried out. In particular, there remains a need for systems which allow enhanced read-length, i.e., the analysis of a greater number of bases in a single lane of a gel, without loss of accuracy or substantial increase in analysis time. It is an object of the present invention to provide a method which answers this need.

SUMMARY OF THE INVENTION

The present invention provides a method for aligning sequence data traces. In accordance with the invention, an experimental data trace representing the positions of a first species of base within a target polynucleotide and a reference data trace representing the positions of a second species of base (which may be the same as or different from the first species) within a reference polynucleotide are obtained by separating appropriate sequencing fragments generated from the target and reference polynucleotides in a common lane of an electrophoresis gel. For each reference data trace, a plurality of peaks corresponding to fragments having a size in the range of 40 to 1200 bases are selected. A base number is assigned to each of the selected peaks in the reference data trace, and a numerical "peak file" is created with information about the peak number and migration time (or distance). This peak file is analyzed to determine a set of polynomial coefficients which will allow substantial linearization of a plot of peak number versus separation between adjacent peaks and alignment of the traces with respect to each other. These coefficients are used to create a corrected time scale identifying where peaks should be located on a given experimental gel. This corrected time scale is used to guide the sampling of the experimental data, and for assignment of peaks within the data.

BRIEF DESCRIPTION OF THE DRAWINGS

FIG. 3A corresponds to the run time difference in the raw data; FIG. 3B is the run time difference after alignment;

DETAILED DESCRIPTION OF THE INVENTION

The present invention provides a method for linearization and alignment sequence data traces. As used herein, the term "linearize" refers to establishing equal spacing in a time domain between adjacent peaks within the overall sequence in an experimental data trace. The term "align" refers to establishing the correct positions within the overall sequence for the peak in an experimental data trace. When a data trace is obtained for each of the four bases, the alignment process results in an explicit determination of the position of each and every base. However, since in some instances it is not necessary to perform all four sequencing reactions and analyze the results to obtain useful diagnostic data, "alignment" can be performed on a single trace, representing the positions of a single species of nucleotide base within a target polynucleotide. In this case, the single trace after linearization is "aligned" with a standard time scale, to show the base numbers associated with peaks within the linearized trace. Alignment can also be performed on data sets of two or more traces representing the positions of two or more species of nucleotide bases within the target polynucleotide.

The process of linearization and alignment is essentially one of assigning a correct numerical position to each of the bases. An important aspect of the linearization and alignment process is compensation for variation in peak spacing which occurs over time even within a single lane of an electrophoresis gel. The present invention performs this compensation by co-electrophoresing a reference sequence with the experimental sequence and utilizing the resulting reference data trace to define the correct peak spacing.

The specification and claims of this application use the term "DNA sequencing fragments" to describe the mixture of polynucleotides which results when chain extension polymerization is performed in the presence of a chain-terminating base analog, such as a dideoxynucleotide triphosphate. The term "DNA sequencing fragments" only requires the presence in the mixtures of fragments the lengths of which are indicative of the positions of one type of base within the polynucleotide being analyzed.

In the simplest embodiment of the invention, experimental and reference data traces obtained from a single lane of an electrophoresis gel are evaluated. The experimental polnucleotide may be, for example, the A-sequencing fragments generated from a target polynucleotide of interest. The reference sample is, for example, the T-sequencing fragments generated from a reference polynucleotide of known sequence. Preferably, the reference polynucleotide is of similar total length to the experimental polynucleotide so that the reference data extends over the entire length of the experimental sequence information.

Because the reference polynucleotide has a known sequence, it is possible to immediately create a peak table having two columns: actual retention time and peak number. Thus, for example, if the sequence were 9 bases long, and had the sequence ACATTACGA, then the data trace derived from the A-sequencing fragment would have four peaks appearing at times $T_1$, $T_2$, $T_3$ and $T_4$, respectively. The peak table would therefore appear as follows:

| | |
|---|---|
| $T_1$ | 1 |
| $T_2$ | 3 |
| $T_3$ | 6 |
| $T_4$ | 9 |

Figure 1:
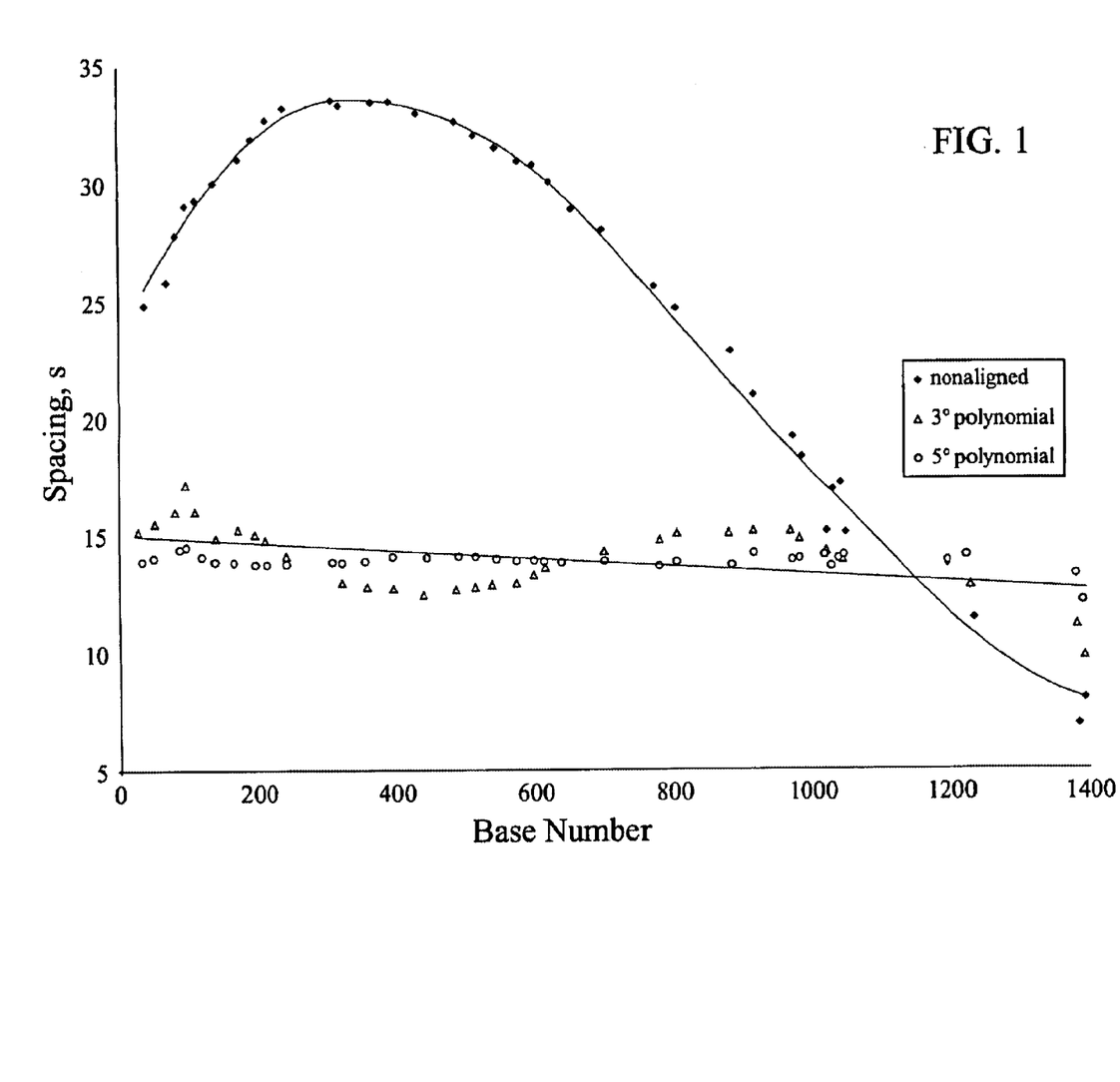
FIG. 1 shows a plot of peak spacing versus peak number for unaligned data, and data aligned with third and fifth order polynomials.

If the spacing of the peaks in the gel over this region were exactly the same, then a plot of T versus peak number would produce a straight line, and a plot of the spacing (the difference between each adjacent peak) versus peak number would produce a straight, horizontal line. Because experimental data does not meet this ideal, however, the result is in fact far different. Thus, as shown in FIG. 1, the experimental spacing between adjacent peaks as a function of base number may follow a complex curve, at first increasing through a maximum, and then decreasing again.

In accordance with the present invention, a curve fitting procedure is applied to the raw reference data trace in which the data is fit to a polynomial, generally a third or higher-order polynomial. Although this fitting process is generally performed in actual practice using a computer program and any of various known curve fitting programs, the procedure employed can be understood from the discussion below. In the unaligned data, one is essentially plotting the function $$\Delta T = mP + c$$

where $\Delta T$ is the spacing between adjacent peaks (in units of time), m is the slope of the line, c is a constant which is characteristic of the gel and which reflects the characteristic peak spacing, and P is peak number. In ideal data, the slope m is 0, such that there is no actual relationship between $\Delta T$ and P, and $\Delta T$ is simply a constant. As one can see in FIG. 1, the experimental data are far from being a straight line. In this case, the experimental curve can be approximated by a polynomial. The empirical curve $\Delta T$ is fit to a polynomial function by a least squares method:

$$\Delta T = a_{i0} + a_{i1}P + a_{i2}P^2 + \ldots + a_{ik}P^k.$$

The degree (k) of the polynomial is an input parameter of the fitting program. The procedure generates a set of coefficient $\{a_{ik}\}$ for each gel lane (i). A curve fitting program identifies the coefficients, $a_i$, (which may be positive or negative) and the constant $a_0$ which bring the resulting plot of the reference data closest to a straight line. Based on the set of polynomial coefficients, $a_{ik}$), a corrected time scale is defined for each peak in gel lane #i, according to the formula $$T_{ip} = C[a_{i0} + a_{i1}t_{ip}P + a_{i2}t_{ip}P^2 + \ldots + a_{ik}t_{ip}P^k],$$

where $T_{ip}$ is the corrected time value for the reference peak of length p, $t_{ip}$ is the experimentally measured run time of this peak, and $C_i$ is a scaling factor. This transformation causes the spacing between consecutive peaks in the corrected time domain ($dT_{ip}/dp$) to remain constant over the course of the run. The transformation (linearization) is performed for both the reference peaks and the sample peaks in each gel lane (i).

Each gel lane has a different scaling factor, $C_i$. For any particular gel, the set of values $\{C_i\}$ is chosen to equalize the spacing between consecutive peaks in the corrected time domain, ($dT_{ip}/dp$), across all lanes of the gel. A gel lane is uniformly compressed by setting $C_i<1$, and it is uniformly stretched by setting $C_i>1$. A set of coefficients ($C_i$) is therefore defined, such that all lanes of the gel have the same total run time in the correct time domain. In the dimension of real time, the data points are evenly spaced. However, in the dimension of "corrected time", the corresponding time intervals are not of equal lengths. Therefore the experimental data sets are "resampled" into equally-spaced values (in the corrected time domain) by quadratic interpolation. Resampling of the data set for each gel lane is done separately, because the corrected time scale may be different for each lane. The procedure described above is a global alignment, which precedes any subsequent local alignment by the base calling software. This global alignment procedure is general, and should be compatible with all types of local alignment algorithms.

The basic methodology described above for alignment of a single data trace can also be applied in other embodiments. For example, data can be obtained for all four bases (A,C, G and T) in four lanes, to obtain explicit position information for the complete sequence of a target polynucleotide. In this case, a set of reference sequencing fragments is desirably run in each of the four lanes. Further, in multi-lane gels, it is desirable to run a set of reference sequencing fragments in each lane, regardless of the nature of the experimental samples. If a sequencing apparatus is used that is capable of distinguishing between more than two labels, multiple experimental sets of sequencing fragments may be run in one lane along with a set of reference sequencing fragments. In each case where more than one reference data trace is obtained from a gel, the spacings of all the reference data traces can be combined to produce a single set of coefficients and single characteristic spacing which is applied to all of the experimental data traces from the gel.

Several features are common to all of the various embodiments discussed above. Each set of the experimental sequencing fragments and the reference sequencing fragments are labeled with a distinguishable labels, i.e., the labels on the experimental fragments and reference fragments are different from one another when they are present in the same lane of the gel. The nature of the labels is a matter of choice and compatability with the detection system employed. Suitable labels include radiolabels, chromophores, chromogenic labels and fluorogenic labels. Preferred labels, however, are fluorescent labels compatible with automated multi-dye sequencers. Specific examples of suitable fluorescent labels include cyanine dyes such as Cy5.0 and Cy5.5 (See U.S. Pat. Nos. 4,981,977 and 5,268, 486) and energy transfer dyes (U.S. Pat. No. 5,800,996) and rhodamine dyes (U.S. Pat. Nos. 5,366,860 and 4,855,225).

There is no required relationship between the target polynucleotide and the reference polynucleotide, and it is not mandatory that the same set of reference sequencing fragments be used in all of the lanes of a gel. This is the case because the alignment depends on the measured position of the known bases of the reference trace, but not on the identity of the bases. However, the reference polynucleotide should be selected to provide enough peaks (or bands) to facilitate the use of a desirable degree of polynomial for fitting the experimental data. For example, if one wishes to use a 5th-degree polynomial, the reference polynucleotide must provide at least 6 peaks.

Furthermore, while it is necessary to know the sequence of the reference polynucleotide for the creation of the initial peak table, it is not necessary to have any a-priori knowledge of the sequence of the target polynucleotide. Thus, while the present invention is particularly applicable to diagnostic applications where the putative sequence of the target polynucleotide is known, it is not limited to such applications.

A further factor which can be adjusted by the user is the number of peaks within the reference data trace that are used in determining the polynomial coefficients and characteristic spacing. While all of the peaks can be considered, this increases the processing time and burden. As a practical matter, a much smaller number of peaks can be utilized and still provide good alignment of the experimental data traces. For example, for alignment of sequencing fragments spanning 40 to 1,200 bases, from 3 to 40 peaks in the reference data trace are suitably selected. The selected peaks are preferably distributed fairly evenly throughout the reference data trace, although precisely equal distribution is not required.

Figure 6:
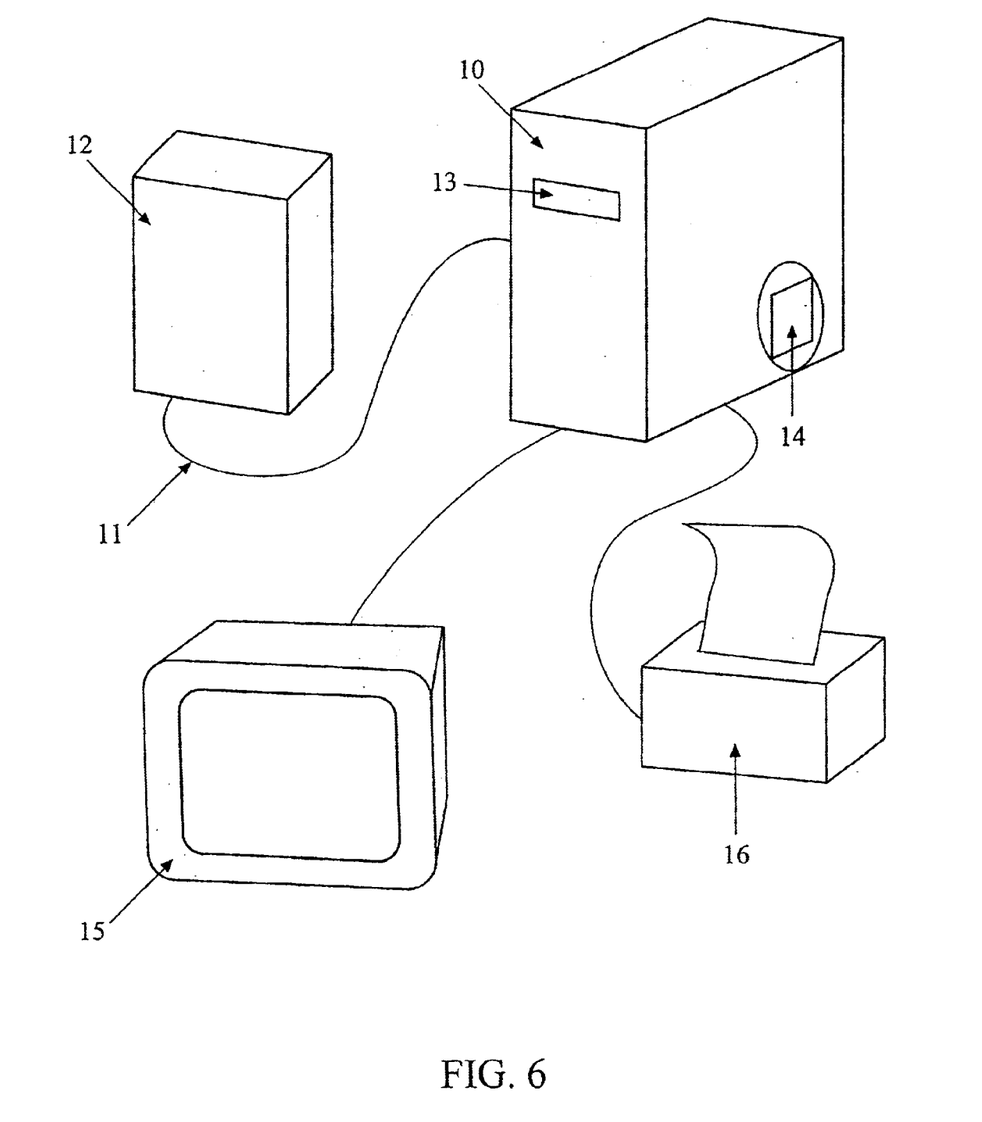
FIG. 6 shows a system in accordance with the invention.

FIG. 6 shows a schematic representation of an apparatus in accordance with the present invention for evaluating the sequence of a target polynucleotide. The apparatus as shown comprises a processor housing 10 which has an input 11 for receiving information from a sequencer 12 about one or more experimental DNA sequencing data traces derived from the separation of experimental DNA sequencing fragments reflecting the position of at least one base in the target polynucleotide and one or more reference DNA sequencing data traces derived from the separation of reference DNA sequencing fragments reflecting the position of at least one base in a reference polynucleotide of known sequence. For example, input 11 may be in the form of a wire for transmitting sequence-related data from a sequencer. Data could also be transmitted via a wireless link, or communicated to the apparatus through disk drive 13.

Within the housing 10 is a data processing apparatus 14 which include one or several processors. The processors or processors are operatively programmed (a) to evaluate the reference DNA sequencing data traces to determine a corrected time scale indicative of migration times at which peaks should occur;

(b)) to sample the experimental DNA sequencing data traces at time points determined by the corrected time scale; and (c) to assign a base number to each peak found in the experimental DNA sequencing data traces based upon the corrected time scale, thereby obtaining information about the sequence of the target polynucleotide. The assigned base numbers may be further processed to provide an output indicative of information about the sequence of the target polynucleotide and this information is communicated to the user via an output device. Exemplary output devices are a display 15 or printer 16. The information may also be communicated by saving it to the disk drive 13 (which can function as either an input or an output device) or through a telecommunication connection (such as a modem or internet connection).

In an embodiment of the invention, the processor programmed to evaluate the reference DNA sequence data traces is programmed to perform the steps of:

(i) identifying a plurality of peaks in the reference DNA sequencing data traces, and creating a data table containing the number of each peak based on the known sequence of the polynucleotide, and the position of each peak in the reference DNA sequencing data trace;

(ii) identifying a set of coefficients for a polynomial effective to substantially linearize a plot of peak number versus separation between adjacent peaks; and (iii) creating from the coefficients and the polynomial a corrected time scale which reflects the positions at which a peak should occur at any given point in a sequencing data trace.

The invention will now be further described and illustrated with reference to the following, non-limiting examples.

EXAMPLE 1

Lanes 1, 5, 9 and 13 of a standard 16 lane MICROCEL™ electrophoresis gel (Visible Genetics Inc.) were loaded with a mixture of the A-terminated sequencing fragments from M13 labeled with CY5.0 fluorescent cyanine dye label as the experimental sample, and T-terminated sequencing fragments from M13 labeled with CY5.5 fluorescent cyanine dye label as the reference sequence. Lanes 2, 6, 10 and 14 were loaded with a mixture of C-terminated sequencing fragments from M13 labeled with CY5.0 fluorescent cyanine dye label as the experimental sample and CY5.5-labeled M13 T's as the reference sequence fragments. Lanes 3, 7, 11 and 15. were loaded with a mixture of G-terminated sequencing fragments from M13 labeled with CY5.0 fluorescent cyanine dye label as the experimental sample and CY5.5-labeled M13 T's as the reference sequence. Lanes 4, 8, 12 and 16 were loaded with a mixture of T-terminated sequencing fragments from M13 labeled with CY5.0 fluorescent cyanine dye label as the experimental sample and CY5.5-labeled M13 T's as the reference sample. The reference sequence and the experimental sequence in this example are derived from the same source, and indeed in the case of the T-terminated sequencing fragments are identical to the reference sequence except for the difference in label. However, the good results for alignment and linearization indicate that the reference sequence does not have to be related to the experimental sequence in any way.

The labeled DNA molecules were separated by electrophoresis and detected using a 638 nm laser excitation source which was detected in real time. The data collection was performed on a 2-color DNA Sequencer (Visible Genetics Inc.), to record two channels for each physical lane, one channel reflecting detection of the CY5.0 label affixed to the experimental sequencing fragments and one channel reflecting detection of the CY5.5 label affixed to the reference fragments. Collected data from the two channels were corrected for overlap in the emission spectra of the two labels and the two resulting data traces were saved as a "data file." Data analysis on the data file was performed using special software in accordance with the protocols of the present invention.

For each reference channel, several peaks (from 3 to 40 in different experiments) were identified having sizes in the range from 40 to about 1200 bases. The base number as assigned to each of these peaks based on knowledge of the sequence of the reference sample, and the position of each peak in the time scale of the experiment was determined. The information about these peaks in the form of a base number and a peak position (or time) was stored in a, "peak file."

To align the raw data stored in the data file, the peak data was used to calculate the standard number of bases per unit time as an average over the 16 reference channels. The data was fit to $3^{rd}$ and $5^{th}$ order polynomials expressing the relationship base number and peak position. Using the fitted polynomial, a corrected time scale was created, so that the reference peaks are equally spaced in the corrected time and have the same origin. The number of bases per unit corrected time is constant for all the data in the run. However, the actual time interval between peaks is not generally constant. Thus, the corrected time scale is used to resample the experimental data trace and the associated reference channel. This procedure essentially involves looking at the experimental at the times specified by the corrected time scale, and determining whether or not a peak is present at the correct time.

Figure 2:
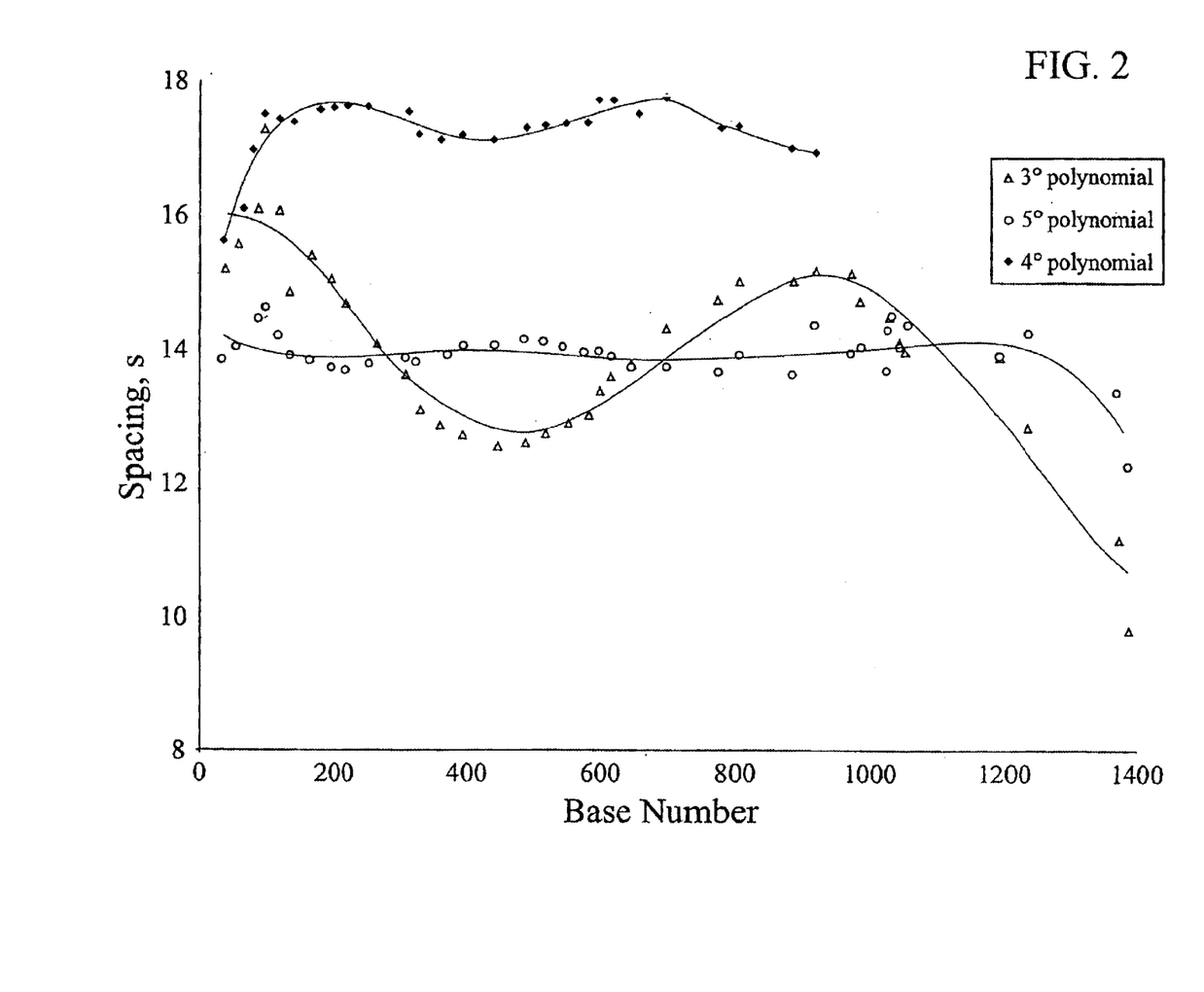
FIG. 2 shows a plot of peak spacing versus peak number for data aligned with third, fourth and fifth order polynomials.

FIGS. 1 and 2 illustrate the application of the invention to the specific sequences described above. An M13 sequence using T-terminated sequencing fragments was performed with T=6% and run at 60° C. on a long gel with a voltage of 1500v. FIG. 1 shows the spacing between adjacent bases as a function of base number, for non-aligned (raw) data (closed diamonds), and data aligned and linearized using a $3^{rd}$ order (open triangles) and $5^{th}$ order (open circles) polynomials. It is clearly seen that the spacing is changing during the run significantly, but is linearized by fitting with either the $3^{rd}$ or $5^{th}$ order polynomial.

FIG. 2 illustrates the influence of the order of the polynomial used for fitting the raw data of the experimental traces. Increasing the polynomial from $3^{rd}$ order (open triangles) to $4^{th}$ order (closed diamonds) improves linearity noticeably, although the curve still have a nonlinear part in the beginning of the run (up to about 100 bases). The $5^{th}$ order polynomial (open circles) gives the best result, with the maximum deviation from the straight line being less than about 0.5 seconds up to 1300 bases. Such linearity is close to the limit in this particular experiment, because the sampling time was 0.5 seconds. Thus, further increase in the order of the polynomial would only increase computational time, without being likely to provide any significant improvement in linearity.

Figure 3A:
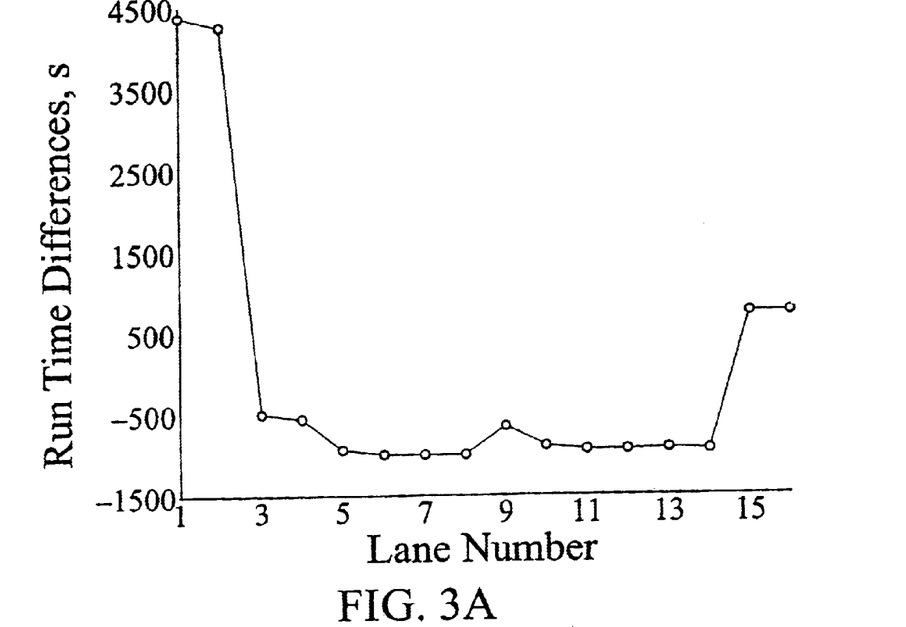
FIGS. 3A and B show plots of the difference, for each lane, between the run time of a base (322nd nt) and its average value for all 16 lanes of a gel.
Figure 3B:
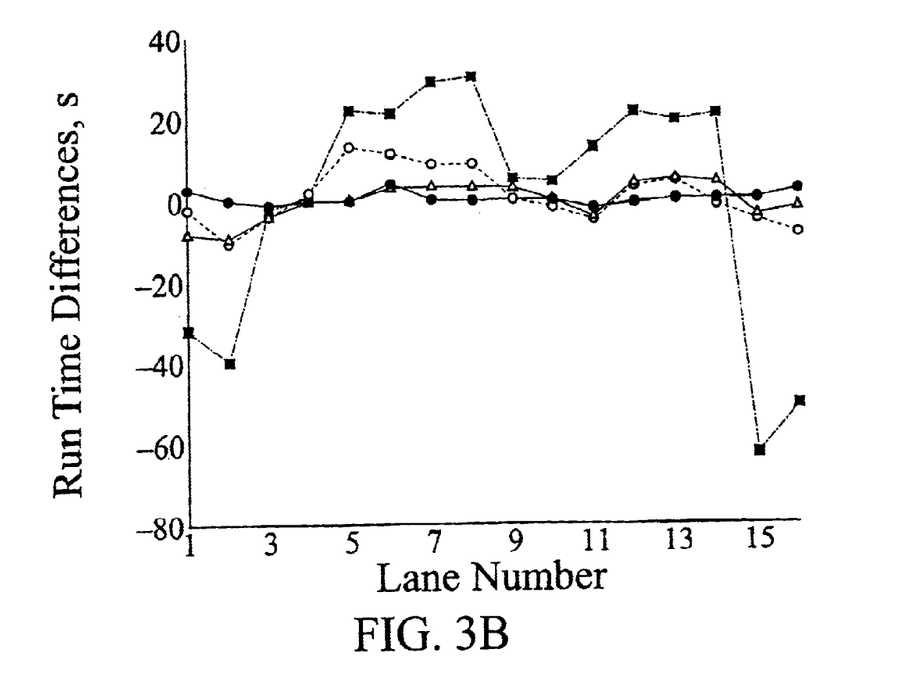

FIGS. 3A and B illustrate improvement in the alignment of the sequencing data (from trace to trace) based on the procedure of the invention. FIG. 3A shows raw data. The difference in run time can reach 500 seconds. Alignment of the raw data, even with a 3rd-degree polynomial, improves the data significantly, reducing the difference in run time to a maximum of ~90 seconds. (See. FIG. 3B) When a 5th-degree polynomial is used, the difference becomes less than 10 seconds.

EXAMPLE 2

Raw data traces were generated using M13 T-terminated sequencing fragments in four adjacent lanes of a sequencing gel. As noted in Table 1, the raw, unaligned data traces showed the substantial variability in peak position that can be observed. Application of a $5^{th}$ order polynomial to this data to determine a corrected time scale, and the application of this time scale to the raw data traces, resulted in a substantial improvement in the alignment of the data. This improved alignment allows the calling of bases with greater accuracy over the entire 1300 bases length.

TABLE 1

| Peak Number | Separation between high and low time peaks, before alignment | Separation between high and low time peaks, after alignment |
|---|---|---|
| 40 | 1 min 16 sec | 14 sec |
| 140 | 2 min 5 sec | 4 sec |
| 312 | 9 min 30 sec | 6 sec |
| 607 | 41 min 38 sec | 4 sec |
| 970 | almost 1.5 hours | 24 sec |

EXAMPLE 3

To understand the significance of the number of peaks incorporated in the peak file for use in generating the polynomial, the data from a T-terminated M13 fragment set was processed using 3, 5, 10, 20 and 40 selected peaks, and the spacing between adjacent peaks at various base positions after alignment was determined. The results are shown in Table 2. As can be seen higher numbers of peaks reduce the extent of variation in peak spacing, although even as few as 3 peaks provides useful results. Comparison of the results from 10, 20 and 40 peaks suggests that an increase beyond 40 would only add to the computational burden without improving the quality of the result.

EXAMPLE 4

To evaluate the ability of the linearization and alignment processes of the invention provide a demonstrable improvement in base calling accuracy and read length, M13 sequence was used. CY5.0-labeled A, C, G and T-terminated sequence fragments were used as experimental samples, while M13 T's labeled with CY5.5 were used as the reference sample. Base-calling was performed on the raw data, and on the data after alignment based on 40 peaks of the reference trace.

TABLE 2

| Base # | uz,9/32 # of Peaks used for Alignment | | | | |
|---|---|---|---|---|---|
| | 3 pk | 5 pk | 10 pk | 20 pk | 40 pk |
| 40 | 10.4 | 14.6 | 15.2 | 14.1 | 15.7 |
| 52 | 11.1 | 15.3 | 15.8 | 14.6 | 16.1 |
| 95 | 12.4 | 16.4 | 16.7 | 15.6 | 17.5 |
| 117 | 13.0 | 16.7 | 16.9 | 15.8 | 17.4 |
| 140 | 13.7 | 16.7 | 16.7 | 15.6 | 17.4 |
| 194 | 15.0 | 16.9 | 15.7 | 15.7 | 17.5 |
| 254 | 16.4 | 16.9 | 16.5 | 15.6 | 17.6 |
| 312 | 17.3 | 16.7 | 16.3 | 15.4 | 17.5 |
| 331 | 17.7 | 16.3 | 16.0 | 15.1 | 17.2 |
| 392 | 18.5 | 16.3 | 16.2 | 15.2 | 17.3 |
| 446 | 19.5 | 16.5 | 16.6 | 15.6 | 17.2 |
| 519 | 19.6 | 16.4 | 16.7 | 15.6 | 17.3 |
| 579 | 19.2 | 16.4 | 16.7 | 15.5 | 17.3 |
| 622 | 18.7 | 16.5 | 16.8 | 15.6 | 17.6 |
| 701 | 18.0 | 16.8 | 16.5 | 15.4 | 17.6 |
| 741 | 17.3 | 16.7 | 16.4 | 15.4 | 17.7 |
| 809 | 16.4 | 16.7 | 16.3 | 15.3 | 17.4 |
| 882 | 15.6 | 17.0 | 16.6 | 15.7 | 17.1 |
| 922 | 15.2 | 16.8 | 16.7 | 15.8 | 17.0 |
| 970 | 14.1 | 16.2 | 16.5 | 15.5 | 17.0 |
| 1026 | 13.4 | 15.7 | 16.5 | 15.4 | 16.9 |
| 1047 | 12.3 | 15.4 | 16.5 | 15.4 | 16.9 |
| Average | 15.7 | 16.3 | 16.4 | 15.4 | 17.2 |
| SQDEV | 7.6 | 0.3 | 0.1 | 0.1 | 0.2 |
| Stndrd. Dev. | 2.8 | 0.6 | 0.4 | 0.4 | 0.5 |
| Max dev. | 9.2 | 2.4 | 1.6 | 1.7 | 2.0 |

Figure 4:
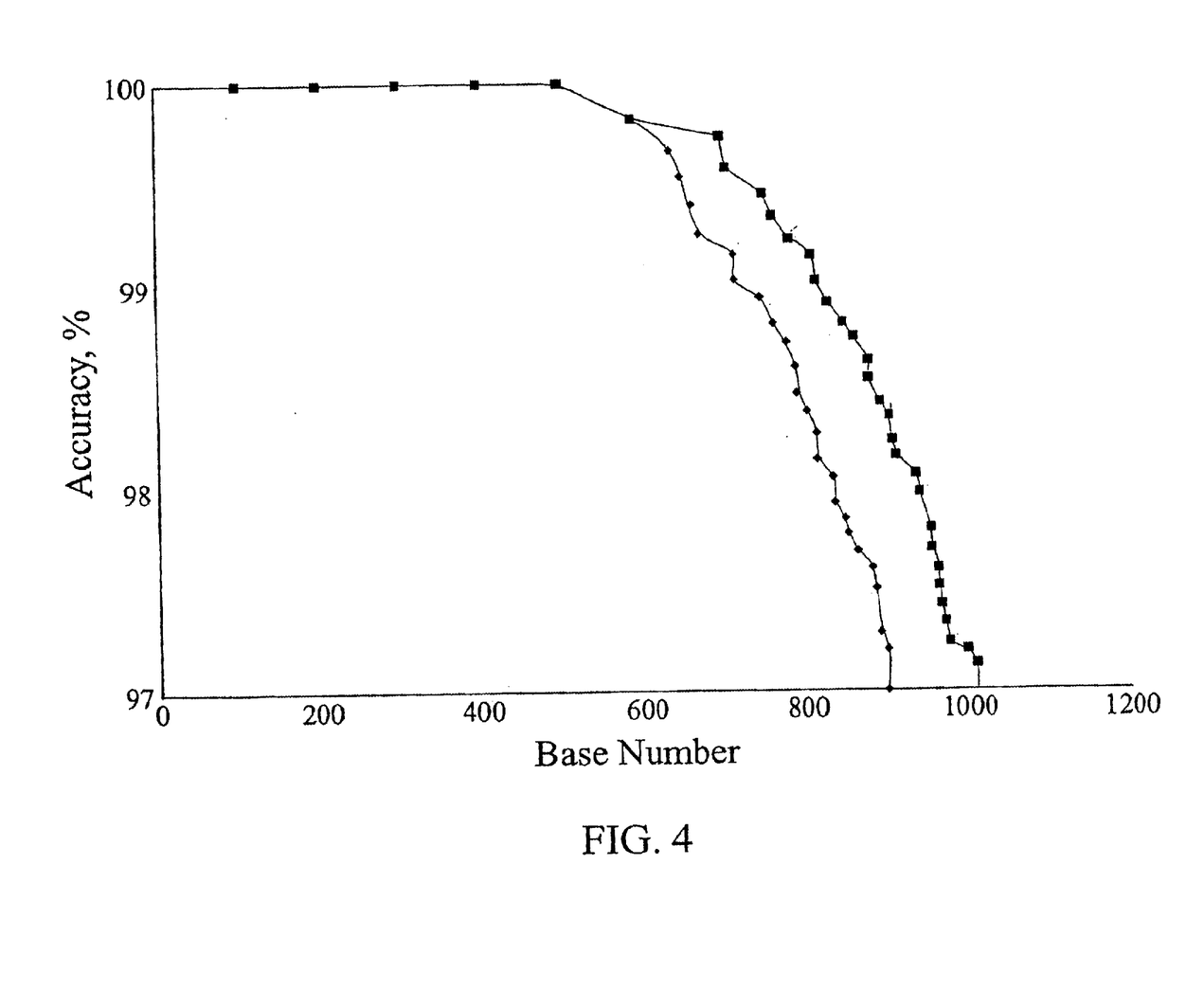
FIG. 4 shows the relationship between accuracy and read length for a first set of experimental data which was well-aligned on the gel.
Figure 5:
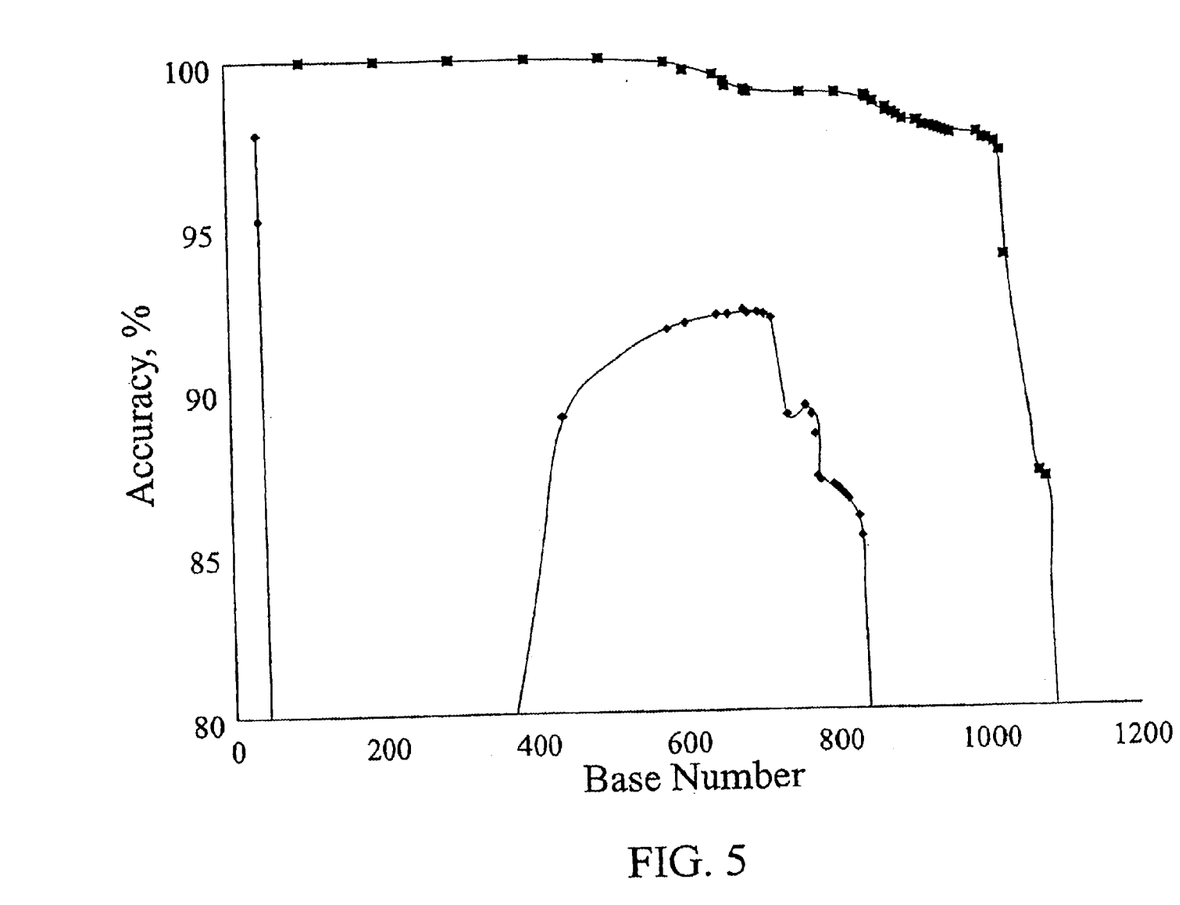
FIG. 5 shows the relationship between accuracy and read length for a first set of experimental data which was poorly-aligned on the gel.

The relationship between accuracy and read length for each of these two experiments is shown in FIGS. 4 and 5, respectively. As shown in FIG. 4, for a given accuracy (for example 97%), data alignment based on information from a reference channel allows increase in read length for at least 10%, i.e., for another 100 bases to be accurately read. Alternatively, for a given read length (for example 900 bases), it provides improved accuracy (98.5% from 97%). These conclusion are based on results of base calling for lanes that were relatively well-aligned to begin with. For channels which experience a large shift in the raw data, the effect of alignment in accordance with the invention is more pronounced. (FIG. 5). Thus, in this experimental system without alignment it is possible to call only 100 bases with reasonable accuracy. After alignment, however, up to 1000 bases can be called.

What is claimed is:

1. A method for assignment of base numbers to peaks within one or more experimental DNA sequencing data traces derived from the separation of experimental DNA sequencing fragments, comprising the steps of:
   (a) obtaining one or more reference DNA sequencing data traces derived from the separation of reference DNA sequencing fragments reflecting the position of at least one base in a reference polynucleotide of known sequence;
   (b) evaluating the reference DNA sequencing data traces to determine a corrected time scale indicative of migration times at which peaks should occur;
   (c) sampling the experimental DNA sequencing data trace(s) at time points determined by the corrected time scale, and
   (d) assigning a base number to each peak found in the experimental DNA sequencing data trace(s) based upon the corrected time scale.

2. The method of claim 1, wherein the step of evaluating the reference DNA sequence data traces includes the steps of:
   (i) identifying a plurality of peaks in the reference DNA sequencing data traces, and creating a data table containing the number of each peak based on the known sequence of the polynucleotide, and the position of each peak in the reference DNA sequencing data trace;
   (ii) identifying a set of coefficients for a polynomial effective to substantially linearize a plot of peak number versus separation between adjacent peaks; and
   (iii) creating from the coefficients and the polynomial a corrected time scale which reflects the positions at which a peak should occur at any given point in a sequencing data trace.

3. The method of claim 2, wherein the polynomial is a third or higher order polynomial.

4. The method of claim 2, wherein a defined number of bands are selected for evaluation from each of the reference DNA sequencing data traces.

5. The method of claim 4, wherein the defined number of bands selected is from 3 to 40.

6. The method of claim 4, wherein the defined number of bands is at least equal to the order of the polynomial, plus 1.

7. The method of claim 1, wherein the experimental DNA sequencing data traces and a first reference DNA sequencing data trace are derived from analysis of sequencing fragments in a common lane of a sequencing gel.

8. The method of claim 1, wherein a plurality of reference DNA sequencing data traces are obtained, each derived from the separation of the same set of reference DNA sequencing fragments.

9. The method of claim 1, wherein base numbers are assigned to peaks within a plurality of experimental DNA sequencing data trace derived from the separation of experimental DNA sequencing fragments indicative of the positions of a plurality of types of bases.

10. The method of claim 9, wherein base numbers are assigned to peaks within four experimental DNA sequencing data traces derived from the separation of experimental DNA sequencing fragments indicative of the positions of four types of bases.

11. A method for evaluating the sequence of a target polynucleotide, comprising the steps of:
   (a) obtaining one or more experimental DNA sequencing data traces derived from the separation of experimental DNA sequencing fragments reflecting the position of at least one base in the target polynucleotide and one or more reference DNA sequencing data traces derived from the separation of reference DNA sequencing fragments reflecting the position of at least one base in a reference polynucleotide of known sequence;
   (b) evaluating the reference DNA sequencing data traces to determine a corrected time scale indicative of migration times at which peaks should occur;
   (c) sampling the experimental DNA sequencing data traces at time points determined by the corrected time scale, and
   (d) assigning a base number to each peak found in the experimental DNA sequencing data traces based upon the corrected time scale, thereby obtaining information about the sequence of the target polynucleotide.

12. The method of claim 11, wherein the step of evaluating the reference DNA sequence data traces includes the steps of:
   (i) identifying a plurality of peaks in the reference DNA sequencing data traces, and creating a data table containing the number of each peak based on the known sequence of the polynucleotide, and the position of each peak in the reference DNA sequencing data trace;
   (ii) identifying a set of coefficients for a polynomial effective to substantially linearize a plot of peak number versus separation between adjacent peaks; and
   (iii) creating from the coefficients and the polynomial a corrected time scale which reflects the positions at which a peak should occur at any given point in a sequencing data trace.

13. The method of claim 12, wherein the polynomial is a third or higher order polynomial.

14. The method of claim 12, wherein a defined number of bands are selected for evaluation from each of the reference DNA sequencing data traces.

15. The method of claim 14, wherein the defined number of bands selected is from 3 to 40.

16. The method of claim 14, wherein the defined number of bands is at least equal to the order of the polynomial, plus 1.

17. The method of claim 11, wherein the reference DNA sequencing traces and the experimental DNA sequencing data traces are derived from analysis of sequencing fragments in a common sequencing gel.

18. The method of claim 17, wherein the experimental DNA sequencing data traces and a first reference DNA sequencing data trace are derived from analysis of sequencing fragments in a common lane of the common sequencing gel.

19. The method of claim 11, wherein a plurality of reference DNA sequencing data traces are obtained, each derived from the separation of the same set of reference DNA sequencing fragments.

20. The method of claim 11, wherein base numbers are assigned to peaks within a plurality of experimental DNA sequencing data traces derived from the separation of experimental DNA sequencing fragments indicative of the positions of a plurality of types of bases.

21. An apparatus for evaluating the sequence of a target polynucleotide, comprising:
   (a) an input for receiving information about one or more experimental DNA sequencing data traces derived from the separation of experimental DNA sequencing fragments reflecting the position of at least one base in the target polynucleotide and one or more reference DNA sequencing data traces derived from the separation of reference DNA sequencing fragments reflecting the position of at least one base in a reference polynucleotide of known sequence;
   (b) a processor, operatively programmed to evaluate the reference DNA sequencing data traces to determine a corrected time scale indicative of migration times at which peaks should occur;
   (c) a processor, operatively programed to sample the experimental DNA sequencing data traces at time points determined by the corrected time scale;
   (d) a processor, operatively programmed to assign a ba number to each peak found in the experimental DNA sequencing data traces based upon the corrected time scale, thereby obtaining information about the sequence of the target polynucleotide; and
   (e) an output for communicating the information about the sequence of the target polynucleotide.

22. The apparatus of claim 21, wherein the processor programmed to evaluate the reference DNA sequence data traces is programmed to perform the steps of:
   (i) identifying a plurality of peaks in the reference DNA sequencing data traces, and creating a data table containing the number of each peak based on the known sequence of the polynucleotide, and the position of each peak in the reference DNA sequencing data trace;
   (ii) identifying a set of coefficients for a polynomial effective to substantially linearize a plot of peak number versus separation between adjacent peaks; and
   (iii) creating from the coefficients and the polynomial a corrected time scale which reflects the positions at which a peak should occur at any given point in a sequencing data trace.

* * * * *